(12) United States Patent
Sakakibara et al.

(10) Patent No.: US 6,599,712 B1
(45) Date of Patent: Jul. 29, 2003

(54) METHOD AND APPARATUS FOR MEASURING SAMPLE BY LUMINESCENCE

(75) Inventors: Tatsuya Sakakibara, Noda (JP); Toshinori Igarashi, Noda (JP); Seiji Murakami, Noda (JP); Yasushi Haketa, Sayama (JP)

(73) Assignee: Kikkoman Corporation, Chiba-ken (JP)

( * ) Notice: Subject to any disclaimer, the term of this patent is extended or adjusted under 35 U.S.C. 154(b) by 0 days.

(21) Appl. No.: 09/869,218

(22) PCT Filed: Dec. 24, 1999

(86) PCT No.: PCT/JP99/07276

§ 371 (c)(1),
(2), (4) Date: Jul. 24, 2001

(87) PCT Pub. No.: WO00/40748

PCT Pub. Date: Jul. 13, 2000

(30) Foreign Application Priority Data

Dec. 28, 1998 (JP) .............................. 10-373290
Dec. 21, 1999 (JP) .............................. 11-362071

(51) Int. Cl.$^7$ .......................... C12Q 1/50; C12Q 1/66; C12M 1/00; C12M 1/34

(52) U.S. Cl. ........................ 435/17; 435/8; 435/283.1; 435/287.1; 435/288.7

(58) Field of Search ......................... 435/17, 8, 283.1, 435/287.1, 288.7

(56) References Cited

U.S. PATENT DOCUMENTS 4,349,510 A * 9/1982 Kolehmainen et al. ...... 435/968

FOREIGN PATENT DOCUMENTS

| JP | 62-269023 | 11/1987 |
| JP | 07-059555 | 3/1995 |
| JP | 09-234099 | 11/1997 |
| WO | 90/04775 | 5/1990 |

* cited by examiner

*Primary Examiner*—Louise N. Leary
(74) *Attorney, Agent, or Firm*—Merchant & Gould, P.C.

(57) ABSTRACT

A method for measuring stains of a test sample by measuring adenosine phosphates. Luminescence of the adenosine phosphates is induced by a luminescent reagent (33) containing an ATP regenerating enzyme. The level or quantity of luminescence is detected by a silicon photodiode (5) to thereby measure the stains.

8 Claims, 4 Drawing Sheets

METHOD AND APPARATUS FOR MEASURING SAMPLE BY LUMINESCENCE

TECHNICAL FIELD

This invention relates to a method and an apparatus for testing a sample for adenosine phosphates by causing the sample to react with a luminescent reagent containing an ATP regenerating enzyme.

BACKGROUND ART

It is known that stains produced by bacteria or food can be detected by detecting adenosine triphosphate (ATP) by a luminescent reaction using an appropriate reagent with luciferase. It, however, produces only a small output of light and it has hitherto been usual to use a photomultiplier for a photodetector to obtain a measurable output. The photomultiplier, however, requires a transformer and safety measures, since it needs a high voltage. Therefore, the apparatus as a whole is undesirably large and expensive.

There is also known a photodetector employing an avalanche photodiode (WO90/04775). The apparatus, however, requires a temperature stabilizing system for the avalanche photodiode which necessitates a working temperature of 0 to 5 deg. C. The system has a heat pump based on the Peltier effect and installed adjacent to the photodiode and is supplied with an electric current from a temperature control circuit to cool the photodiode. Therefore, the apparatus is undesirably complicated and expensive.

Therefore, we, the inventors of this invention, have paid attention to silicon photodiodes which do not require any high voltage or current source, and are not affected by temperature. The silicon photodiodes are, however, relatively low in sensitivity and do not always detect ordinary bioluminescence easily.

Some of us have proposed an invention entitled "A bioluminescent reagent and a method of assaying for adenosine phosphates by using the reagent and a method of assaying for substances concerning an ATP transformation system by using the reagent" as disclosed in Japanese Patent Laid-Open Publication No. HEI-9-234099. This invention is a method for detecting adenosinephosphates by a luminescent reaction of high sensitivity employing as a bioluminescent reagent at least a reagent containing an ATP regenerating enzyme, such as pyruvate orthophosphate dikinase, EC 2. 7. 9. 1. (hereinafter referred to as PPDK).

After further research work, we have discovered that adenosine phosphates, or stains can be detected by a simple apparatus if they are detected by measuring the quantity of light produced by the phosphates as a result of their reaction with a luminescent reagent containing an ATP regenerating enzyme, such as PPDK, and if the quantity of light is measured by a silicon photodiode.

DISCLOSURE OF THE INVENTION

According to a first aspect of this invention, there is provided a method for testing a sample by luminescence, which method comprises the steps of reacting the sample with a luminescent reagent containing an ATP regenerating enzyme to cause adenosine phosphates to produce light, and measuring the quantity of such light by a silicon photodiode.

According to a second aspect of this invention, there is provided an apparatus for testing a sample by luminescence, which apparatus comprises an inspecting device housed in a housing chamber, a silicon photodiode for receiving light from the inspecting device, and an operating system for processing the output signal of the photodiode to express the quantity of such light numerically.

More particularly, there is provided an apparatus for detecting stains, which comprises a chamber for housing an inspecting device for taking a sample of stains and causing them to produce light, a silicon photodiode for receiving such light, an operating system for determining the quantity of such light, a control panel and a display panel.

A silicon photodiode is a semiconductor device which responds to even a low level of light and outputs a measurable electrical signal, though it may be somewhat less sensitive to light than a photomultiplier. It does not require any high voltage or current source for its circuit, but is operable with a battery. It does not require any temperature stabilizing device, either, since it is less likely to be affected by any temperature variation than any other diode, such as an avalanche photodiode. Moreover, it is stronger than a photomultiplier, and is not adversely affected by exposure to intense light. Therefore, the apparatus of this invention for testing a sample for cleanness is by far smaller in size, lighter in weight and less expensive than any known apparatus.

The luminescent reagent used for the purpose of this invention contains an ATP regenerating enzyme, such as PPDK, and may be used with luciferin, or luciferase. It emits light and maintains a high level of stable luminescence by reacting not only with ATP, but also with adenosine diphosphate (ADP), adenosine monophosphate (AMP) or ribonucleic acid (RNA). Thus, it makes up for the light sensitivity of the silicon photodiode which is somewhat lower than that of the photomultiplier.

The stains in the context of this invention include adenosine phosphates, such as ATP, ADP, AMP and RNA or the like, and preferably refer to stains detected by a cleanness test.

The ATP regenerating enzyme in the context of this invention may be any enzyme catalyzing the reaction for forming ATP from AMP. Examples are phosphoenolpyruvate synthetase, EC 2.7.9.2., and a combination of adenylate kinase, EC 2.7.4.3. and pyruvate kinase, EC 2.7.1.40. PPDK is, however, preferred.

The PPDK used for the purpose of this invention is an enzyme catalyzing the reaction for forming ATP, pyruvic acid and phosphoric acid by acting upon AMP, phosphoenolpyruvic acid and pyrophosphoric acid, respectively, in the presence of a magnesium metal ion. It is easily available, as its physical and chemical properties and processes for its manufacture are already known (see Japanese Patent Laid-Open Publication No. HEI-9-234099).

The luminescent reagent containing an ATP regenerating enzyme may be prepared if, for example, PPDK is added to a luminescent reagent containing luciferin, luciferase and a metal salt, and a still more effective reagent may further contain phosphoenolpyruvic and pyrophosphoric acids. It detects even a small amount of stains by responding not only to ATP as an indicator of stains, but also to AMP. A reagent still further containing an enzyme catalyzing the reaction for forming ATP from ADP and/or an enzyme decomposing RNA detects a still smaller amount of stains by responding not only to ATP and AMP, but also to ADP and RNA.

This invention may be carried out by applying a swab to wipe stains off the surface to be tested, and dipping it in an extraction reagent containing a surface active agent for extracting adenosine phosphates, such as ATP, ADP, AMP and RNA, from stains, such as bacteria, whereby a sample solution is obtained. It is mixed with a luminescent reagent containing an ATP regenerating enzyme, such as PPDK or the like, and the quantity of light emitted by their mixture is measured by a stain testing apparatus, whereby the stains on the surface to be tested are detected. It is preferable to use a cleanness or hygiene monitoring device including the swab and the extraction and luminescent reagents as a unitary set to make the inspection still easier.

A hygiene monitoring or wipe inspecting device including a luminescent reagent containing an ATP regenerating enzyme, such as PPDK, makes a small, lightweight and economical apparatus which ensures a very accurate and reliable test for cleanness. More specifically, the surface to be tested is wiped by a swab in the hygiene monitoring device, the swab is dipped in the extraction reagent in the device, the resulting sample solution is reacted with the luminescent reagent held in the device and containing an ATP regenerating enzyme, such as PPDK, the hygiene monitoring device as a whole is set in the cleanness testing apparatus, and the quantity of light thereby emitted is measured to determine the amount of stains.

According to this invention, the use of a luminescent reagent containing an ATP regenerating enzyme, such as PPDK, ensures a stable emission of intense light detectable even by a silicon photodiode, and thereby makes it possible to realize a small and lightweight testing apparatus.

BEST MODE FOR CARRYING OUT THE INVENTION

Certain preferred embodiments of this invention will now be described in detail with reference to the accompanying drawings.

Figure 1:
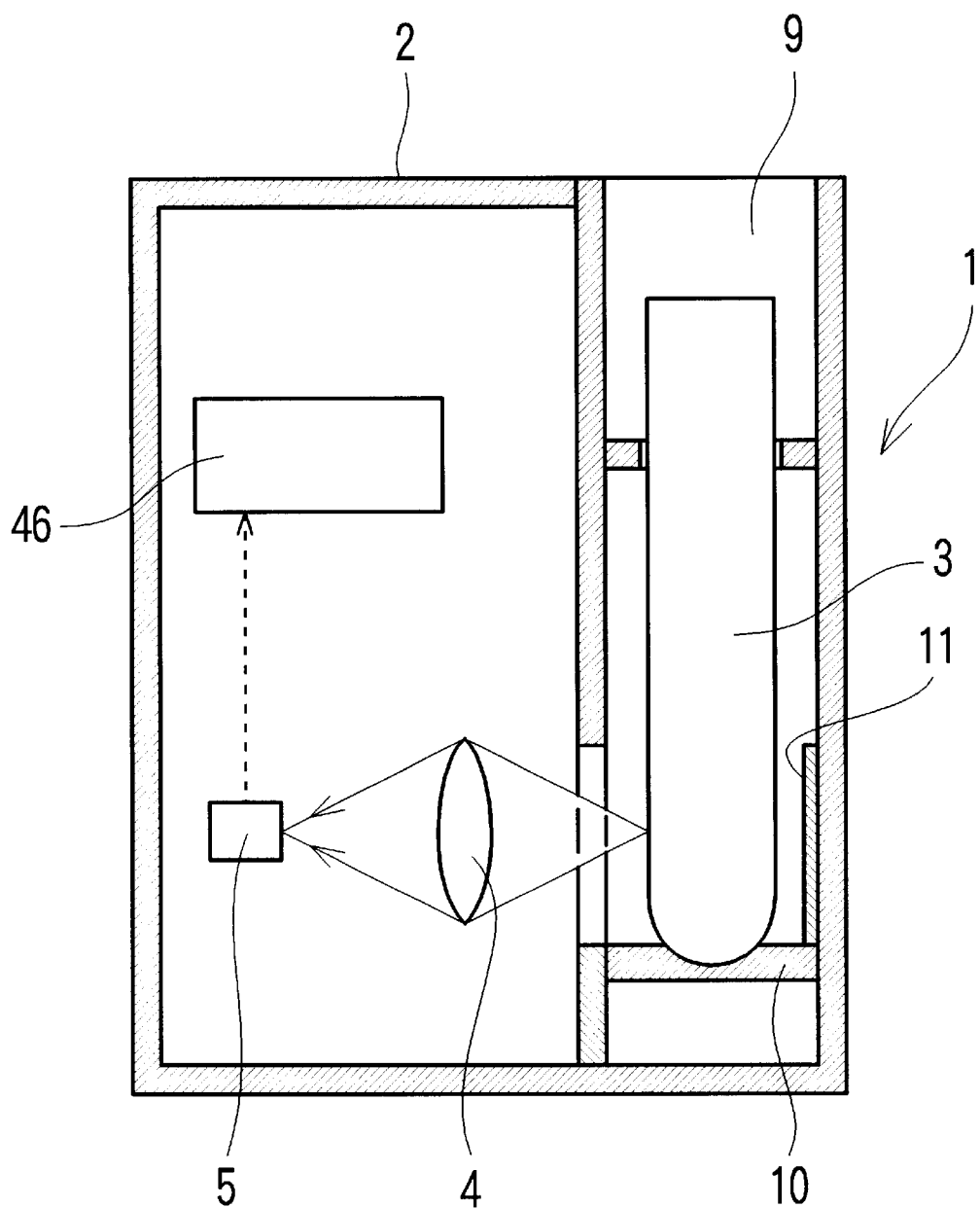
FIG. 1 is a schematic cross-section diagram, partly in section, of a stain testing apparatus.

Referring to FIG. 1, a stain testing apparatus 1 has a main body 2 as a housing. The main body 2 houses a hygiene monitoring or wipe inspecting device 3 for scraping stains off and causing them to undergo a bioluminescent reaction, a condenser lens 4 for condensing light from the device 3, a silicon photodiode 5 for converting the light from the lens 4 to an electrical signal, and an operating system 46 for processing the electrical signals from the photodiode 5.

Figure 2:
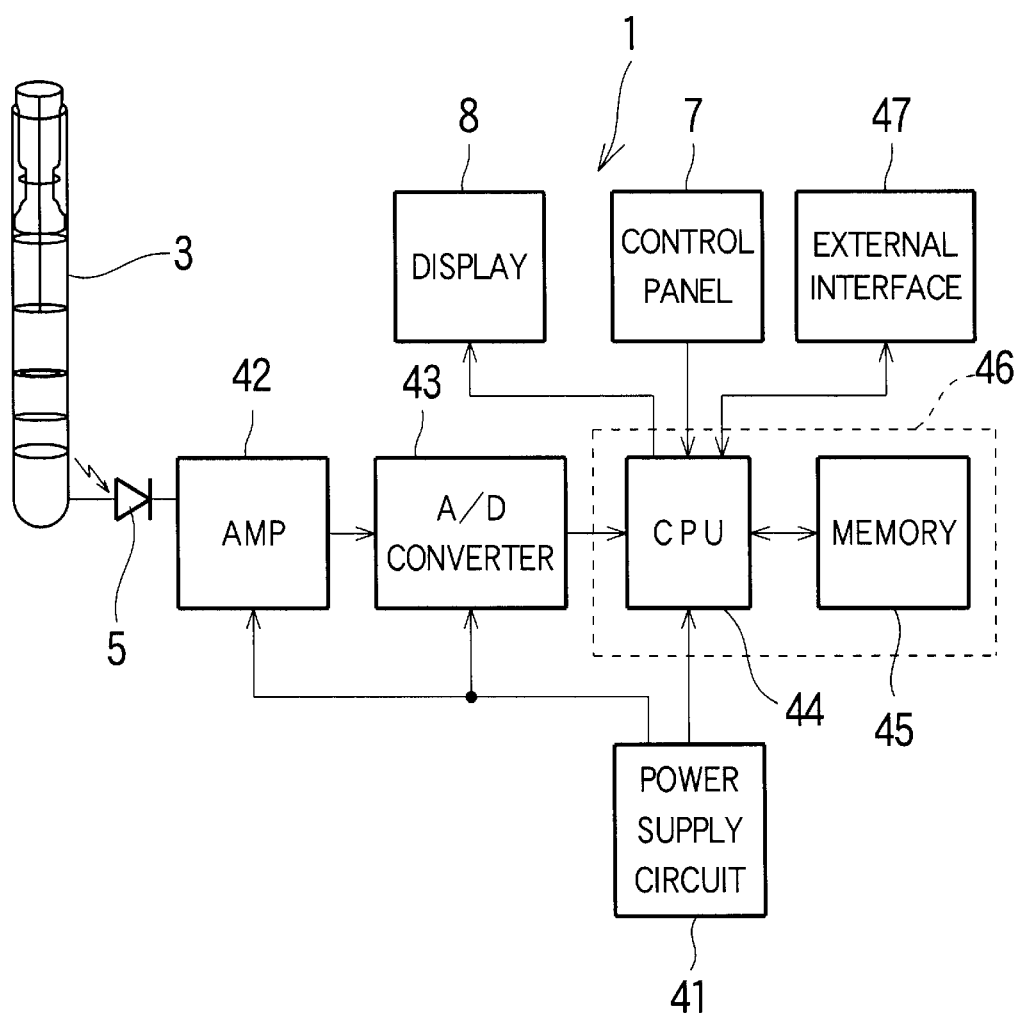
FIG. 2 is a block diagram including a specific example of an operating system.
Figure 3:
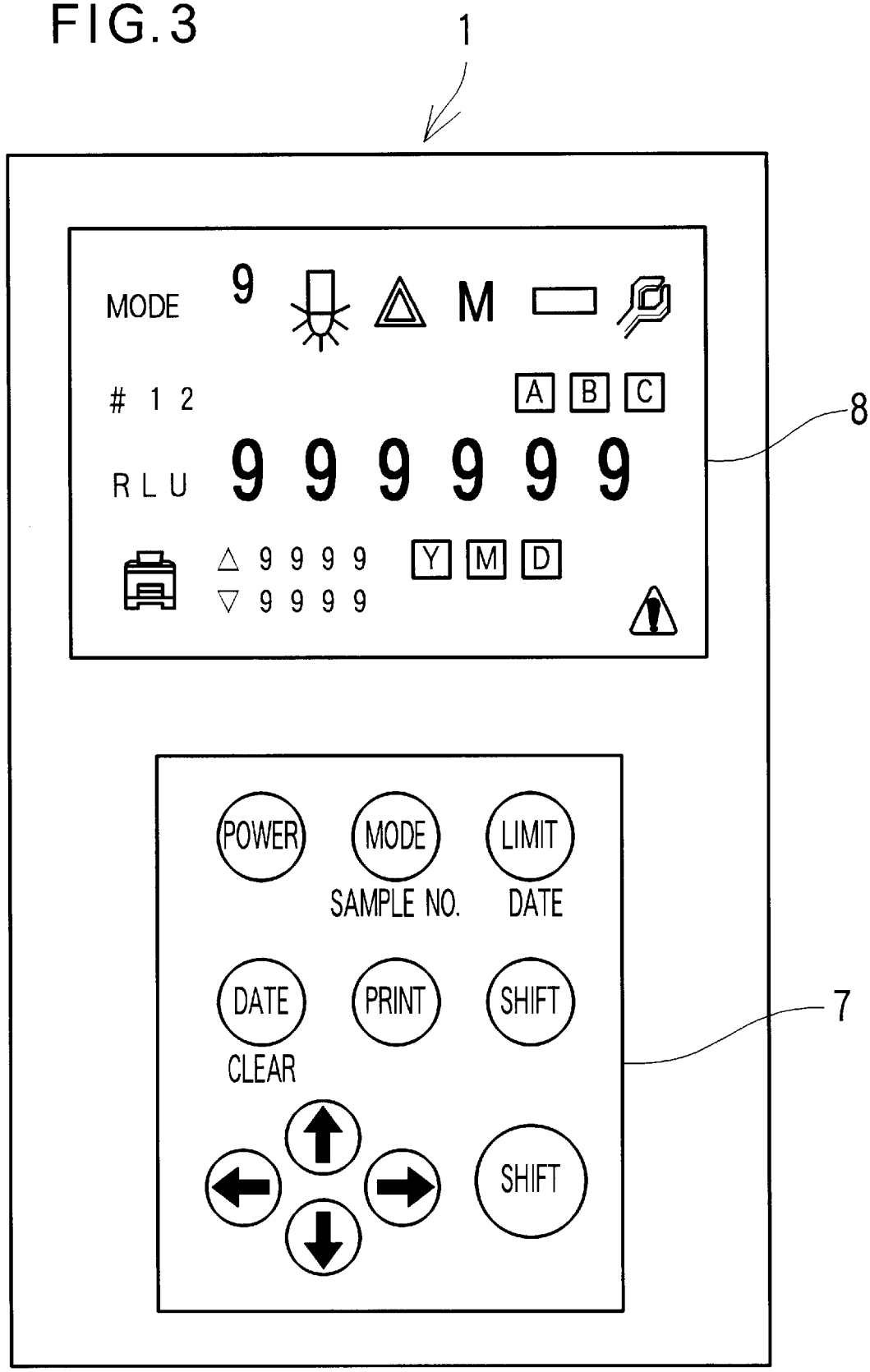
FIG. 3 is a front elevational view of the apparatus showing a display and a control panel.

The main body 2 is also provided with a control panel 7 and a display panel 8, as shown in FIG. 3. The control and display panels 7 and 8 are electrically connected to the operating system 46, as shown in FIG. 2. The control panel 7 indicates detailed instructions for a particular test. The display panel 8 displays the test results.

The main body 2 has a chamber 9 for housing the hygiene monitoring device 3. The chamber 9 has a table 10 on which the device 3 is mounted and held in position. A reflecting mirror 11 is situated behind the device 3 for transmitting as large a quantity of light as possible to the photodiode 5 through the lens 4.

FIG. 2 is a block diagram showing the electrical performance of the apparatus 1 shown in FIG. 1. The apparatus 1 has a power supply circuit 41, an amplifier 42, an analog-to-digital converter 43, the operating system 46, the control and display panels 7 and 8, and an external interface 47.

The power supply circuit 41 is adapted to receive both a supply of DC power and a supply of AC power.

The amplifier 42 converts the output signal of the photodiode 5 into voltage and increases it in accordance with the intensity of the output signal of the photodiode 5, or the intensity of the light emitted by the inspecting device 3. The output signal of the amplifier 42 is converted into a digital signal by the analog-to-digital converter 43 and the latter is supplied to the operating system 46.

The operating system 46 comprises a central processing unit (CPU) 44 and a memory 45. The central processing unit 44 converts the output signal of the photodiode 5 into a numerical value and sends it to the display panel 8, or compares it with data on the degree of contamination as stored in the memory 45, concludes a value exceeding a threshold as indicating an object requiring cleansing, and sends its conclusion to the display panel 8.

The control panel 7 is provided for effecting the storage of test data, transmission of the data to a printer or a distant place through the interface 47, and inputting of such data in the memory 45.

Figure 4:
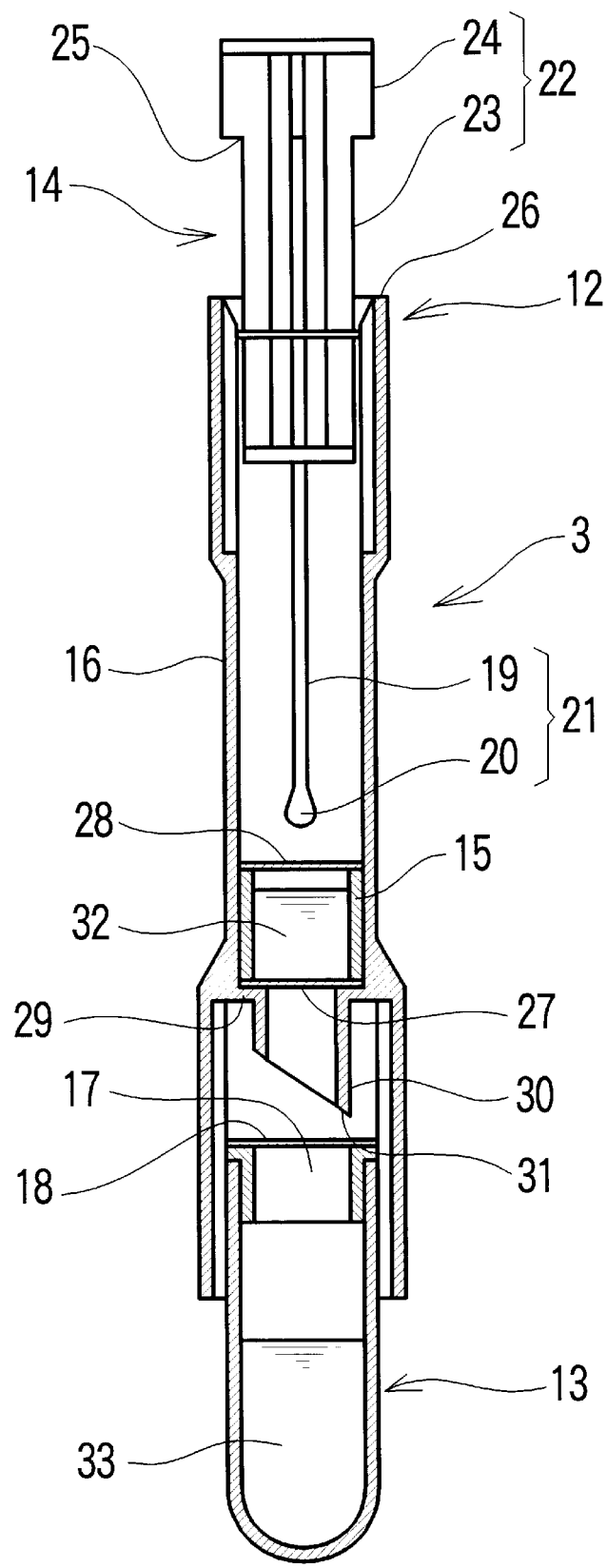
FIG. 4 is a detailed view, partly in section, of a hygiene monitoring device.

The hygiene monitoring device 3 may be constructed as shown in FIG. 4, though it may be of any other construction if it employs a luminescent reagent containing an ATP regenerating enzyme, such as PPDK. The device 3 is mainly composed of a sampler 12 and a luminescent reagent container 13 shaped like a test tube. The sampler 12 is composed of a sample wiper 14, an extraction agent container 15 and a tubular main body 16. The luminescent reagent container 13 is tightly closed, as its opening 17 is closed by a sealing member 18 formed from, for example, an aluminum foil.

The sample wiper 14 is composed of a swab 21 and a swab holding member 22. The swab 21 consists of a rod portion 19 and an egg-shaped wad portion 20 formed at its lower end. The swab holding member 22 has a diametrically small lower portion 23 and a diametrically large upper portion 24. The lower and upper portions 23 and 24 have a shoulder 25 formed therebetween. The shoulder 25 is so formed as to contact the upper end 26 of the main body 16 so that the sample wiper 14 may always stop at a fixed position after its downward movement in the main body 16. The sample wiper 14 is removable from the main body 16. After the swab 21 has been applied to wipe a sample surface, the sample wiper 14 is fitted in the main body 16 so that stains may be collected.

The extraction agent container 15 contains an extraction agent 32 for extracting the stains wiped by the wad portion 20 of the swab 21 off the sample surface. The container 15 is open at both of its top and bottom, and after its bottom is closed by a sealing member 27, the extraction agent 32 is poured into the container 15, and its top is closed by a sealing member 28 to confine the extraction agent 32 in the container. The sealing members 27 and 28 are formed from a material which is easily broken by the swab 21 pressed there against, for example, an aluminum foil.

The main body 16 of the sampler 12 is a tubular member which is open at its top and bottom. The main body 16 has an annular projection 29 formed on the inner wall surface of its lower portion. An anti-scattering extension 30 projects downwardly from the projection 29. The anti-scattering extension 30 has a sharp-angled portion 31 adapted to tear the sealing member 18 if the luminescent reagent container 13 is thrust upwardly, so that the extraction agent containing the stains extracted from the wad portion 20 may drop into the container 13, in which the stains are detected by a luminescent reaction.

Description will now be made of the performance of the hygiene monitoring device 3. The sample wiper 14 is first removed from the main body 16 and the wad portion 20 is applied to wipe stains off a sample surface. Then, the sample wiper 14 is fitted in the main body 16 and the luminescent reagent container 13 is thrusted upwardly to have the sealing member 18 broken by the sharp-angled portion 31 of the anti-scattering extension 30. Then, the sample wiper 14 is forced down to have the swab 21 break the sealing member 28, so that its wad portion 20 may enter the extraction agent container 15. The wiper 14 is further lowered until the shoulder 25 of the swab holding member 22 contacts the upper end 26 of the main body 16, whereupon the swab 21 breaks the sealing member 27. Then, the device 3 as a whole is moved up and down lightly to allow the extraction agent 32 containing bacteria or stains to drop into the container 13 and mix with the luminescent reagent 33, so that a luminescent reaction may take place to produce light. Then, the device 3 is placed in the chamber 9 of the stain testing apparatus 1, so that the quantity of light, or the amount of stains may be determined. The luminescent reagent 33 in the device 3 contains an ATP regenerating enzyme, such as PPDK.

While the foregoing description has been concerned with a sample taken by scraping, it is also possible to place a sample liquid, solid, or powder in a test tube holding a luminescent reagent containing an ATP regenerating enzyme, such as PPDK, to determine the amount of its stains. Moreover, the apparatus of this invention can be used for testing a sample by relying not only upon bioluminescence, but also upon chemical luminescence or fluorescence.

The effects of this invention will now be shown numerically by examples of experiments. The amounts of the enzymes are shown in international units.

EXAMPLE 1

Composition of a Luminescent Reagent Containing PPDK:

EDTA (Ethylenediamine tetraacetate)—1.0 mM

Dithiothreitol—1.0 mM

Ammonium sulfate—3.75 mM

Pyrophosphoric acid—0.3 mM

Phosphoenolpyruvic acid—2.1 mM

Luciferin—0.75 mM

Magnesium sulfate—7.5 mM

BSA (Bovine serum albumin)—0.5%

Sucrose—5.0%

Luciferase—2.5 mg/ml

PPDK—1.5 U/ml

Adenosine phosphate deaminase—0.05 U/ml

HEPES (50 mM)—pH 7.8

Composition of an Extraction Agent:

Benzalkonium chloride—0.02%

HEPES (10 mM)—pH 7.8

A freeze-dried product of the luminescent reagent having the composition shown above and containing PPDK was encapsulated in the luminescent reagent container 13 of a hygiene monitoring device 3 as shown in FIG. 4, and the extraction agent was encapsulated in the container 15. A freeze-dried product of the luminescent reagent having the composition shown above, but not containing PPDK was likewise encapsulated in the luminescent reagent container of another device, while it was the same extraction agent that was encapsulated in its container 15.

Samples representing stains for which food was responsible were prepared by diluting commercially available yeast, beef and malt extracts, beer and cow's milk to various concentrations with ultrapure water. The swab 21 of each hygiene monitoring device 3 was dipped in a sample dilution, and its swab holding member was forced into the device to have the head of the swab dipped in the extraction agent, and was further forced down, so that the extraction agent containing stains might enter the container 13 containing the freeze-dried luminescent reagent and cause luminescence.

Then, each hygiene monitoring device 3 was set in a stain testing apparatus 1 having a silicon photodiode and the quantity of light produced was measured. The results of the measurement are shown in RLU (relative light unit) in Table 1 below.

TABLE 1

Test results obtained on samples by a stain testing apparatus having a silicon photodiode

| Sample | Sample concentration (%) | Quantity of light as measured | |
|---|---|---|---|
| | | With PPDK | Without PPDK |
| Yeast extract | 0.01 | 1117 | 0 |
| Beef extract | 0.001 | 1252 | 0 |
| Malt extract | 0.1 | 37 | 0 |
| Beer | 10 | 453 | 0 |
| Cow's milk | 1 | 116 | 8 |

When the luminescent reagent did not contain PPDK, light was produced only by ATP and its quantity was unstable with a sharp decrease and was zero in most of the cases, as shown in Table 1. If the reagent contained PPDK, however, light was produced not only by ATP, but also by AMP, which is contained in a large quantity in food, and its quantity was stable, thereby enabling a highly accurate assay for stains.

EXAMPLE 2

A rice scoop used for serving boiled rice was lightly rinsed in water and stains were wiped off a surface portion thereof measuring about 10 square centimeters by the swab 21 of each hygiene monitoring device 3 used in Example 1. Then, Example 1 was repeated for causing luminescence and measuring the quantity of light produced. The quantity as measured was 834 RLU when the reagent contained PPDK, while it was zero when the reagent did not contain PPDK.

EXAMPLE 3

The spout of a device for packing an extract of coffee and its vicinity were lightly washed in water and stains were wiped off a spout surface portion measuring about 10 square centimeters by the swab 21 of each hygiene monitoring device 3 used in Example 1. Then, Example 1 was repeated for causing luminescence and measuring the quantity of light produced. The quantity as measured was 675 RLU when the reagent contained PPDK, while it was zero when the reagent did not contain PPDK.

EXAMPLE 4

A noodle cutter in an apparatus for preparing Chinese noodles was lightly washed in water and stains were wiped off a surface portion thereof measuring about 10 square centimeters by the swab 21 of each hygiene monitoring device 3 used in Example 1. Then, Example 1 was repeated for causing luminescence and measuring the quantity of light produced. The quantity as measured was 1,660 RLU when the reagent contained PPDK, while it was zero when the reagent did not contain PPDK.

EXAMPLE 5

The luminescent reagent used in Example 1 and containing PPDK is referred to as a reagent containing PPDK, and the reagent having the same composition, but not containing PPDK as a reagent not containing PPDK. A test tube was loaded with 200 µl of reagent containing PPDK, and another test tube with 200 µl of reagent not containing PPDK, and each test tube was further supplied with 100 µl of a 0.01% dilution of commercially available oolong tea in ultrapure water. Each tube was set in the stain testing apparatus 1 and the quantity of light as produced was measured in relative light unit, or RLU. The quantity as measured was 618 RLU when the reagent contained PPDK, while it was 6 RLU when the reagent did not contain PPDK.

INDUSTRIAL APPLICABILITY

The stain testing apparatus of this invention is portable in a case holding all of the luminescent testing devices, swab, extraction agent and luminescent reagent, and is useful as a cleanness testing kit. The luminescent testing devices are also suitable for testing a wide variety of other samples, for example, raw materials and final products in the food industry, reagents, water and clinical test specimens.

What is claimed is:

1. A method for testing a sample by luminescence, comprising the steps of:

reacting the sample with a luminescent reagent containing an ATP regenerating enzyme to cause adenosine phosphates to produce light; and measuring the quantity of such light by a silicon photodiode.

2. The method of claim 1, wherein the enzyme is pyruvate orthophosphate dikinase.

3. An apparatus for testing a sample by luminescence comprising:

a housing chamber;

an inspecting device housed in the housing chamber;

a silicon photodiode for receiving light from the inspecting device; and an operating system for processing the output signal of the photodiode to express the quantity of such light in a numerical way.

4. The apparatus of claim 3, wherein the inspecting device is designed for hygiene monitoring application.

5. The apparatus of claim 3, wherein the inspecting device comprises a test tube.

6. The apparatus of claim 4, wherein the inspecting device holds a luminescent reagent containing an ATP regenerating enzyme.

7. The apparatus of claim 6, wherein the enzyme is pyruvate orthophosphate dikinase.

8. The apparatus of claim 3, further comprising a control panel and an external interface, said control panel being capable of effecting bi-directional data transmission between said operating system and a distant place through said external interface.

* * * * *